US010010243B2

(12) United States Patent
Abe et al.

(10) Patent No.: US 10,010,243 B2
(45) Date of Patent: Jul. 3, 2018

(54) FLEXIBLE TUBE FOR ENDOSCOPE AND METHOD FOR MANUFACTURING THE SAME

(71) Applicant: FUJIFILM Corporation, Tokyo (JP)

(72) Inventors: Shinya Abe, Ashigarakami-gun (JP); Nobuharu Takahashi, Ashigarakami-gun (JP); Shozo Iyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 528 days.

(21) Appl. No.: 14/667,208

(22) Filed: Mar. 24, 2015

(65) Prior Publication Data
US 2015/0272424 A1    Oct. 1, 2015

(30) Foreign Application Priority Data

Mar. 26, 2014  (JP) ................ 2014-063997

(51) Int. Cl.
*A61B 1/00* (2006.01)
*A61B 1/005* (2006.01)
(Continued)

(52) U.S. Cl.
CPC ............ *A61B 1/0011* (2013.01); *A61B 1/005* (2013.01); *A61B 1/0055* (2013.01);
(Continued)

(58) Field of Classification Search
CPC .......... A61M 25/0053; A61M 25/0054; A61M 25/0013; A61M 25/0021; A61M 25/0045;
(Continued)

(56) References Cited

U.S. PATENT DOCUMENTS

2002/0010386 A1  1/2002  Matsushita et al.
2004/0080613 A1  4/2004  Moriyama
(Continued)

FOREIGN PATENT DOCUMENTS

JP    1-212532 A    8/1989
JP    2005-81100 A  8/1989
(Continued)

OTHER PUBLICATIONS

Extended European Search Report, dated Aug. 10, 2015, for corresponding European Application No. 15159138.5.
(Continued)

*Primary Examiner* — Alexandra L Newton
(74) *Attorney, Agent, or Firm* — Birch, Stewart, Kolasch & Birch, LLP (57) ABSTRACT

A flexible tube for an endoscope includes a flexible tube base, an outer coating layer including a soft resin layer and a hard resin layer, a ratio changing portion, and a tapered portion. In the ratio changing portion, a percentage of a thickness of the hard resin layer decreases and a percentage of a thickness of the soft resin layer increases toward a distal side from a proximal side of the base. In the tapered portion, a ratio between the thickness of the hard resin layer and the thickness of the soft resin layer is maintained, which ratio is the same as that at a position in the ratio changing portion where the percentage of the thickness of the hard resin layer is a lower limit. In the tapered position, an outer diameter of the outer coating layer decreases toward a distal end of the flexible tube base.

10 Claims, 6 Drawing Sheets

(51) Int. Cl.
  *G02B 23/24* (2006.01)
  *B29C 47/00* (2006.01)
  *B29C 47/06* (2006.01)
  *B29L 23/00* (2006.01)

(52) U.S. Cl.
  CPC ...... *A61B 1/00071* (2013.01); *A61B 1/00078* (2013.01); *B29C 47/0026* (2013.01); *B29C 47/06* (2013.01); *G02B 23/2476* (2013.01); *B29L 2023/007* (2013.01)

(58) Field of Classification Search
  CPC .......... A61M 25/0043; A61M 37/0092; A61B 1/00071; A61B 1/0055
  USPC ...................................................... 600/140
  See application file for complete search history.

(56) References Cited

U.S. PATENT DOCUMENTS

| | | | | |
|---|---|---|---|---|
| 2004/0106853 | A1* | 6/2004 | Moriyama | A61B 1/00071 600/140 |
| 2005/0059861 | A1 | 3/2005 | Nishiie | |
| 2010/0075075 | A1* | 3/2010 | Takahashi | A61B 1/00071 428/34.1 |
| 2012/0180896 | A1* | 7/2012 | Takahashi | A61B 1/00078 138/137 |

FOREIGN PATENT DOCUMENTS

| | | |
|---|---|---|
| JP | 2001-190494 A | 7/2001 |
| JP | 2004-141492 A | 5/2004 |
| JP | 2009-106632 A | 5/2009 |
| JP | 2009-226023 A | 10/2009 |
| JP | 2009-226964 A | 10/2009 |
| JP | 2010-75352 A | 4/2010 |

OTHER PUBLICATIONS

Chinese Office Action and Search Report, dated Apr. 24, 2017, for corresponding Chinese Application No. 201510116578.8, with an English translation of the Office Action.
European Patent Office Communication for corresponding European Application No. 15159138.5, dated Aug. 11, 2017.
Japanese Notice of Reasons for Rejection and English translation thereof, dated Mar. 16, 2016, for corresponding Japanese Application No. 2014-063997.

* cited by examiner

FLEXIBLE TUBE FOR ENDOSCOPE AND METHOD FOR MANUFACTURING THE SAME

CROSS-REFERENCE TO RELATED APPLICATIONS

The present application claims priority under 35 U.S.C. § 119 to Japanese Patent Application No. 2014-063997, filed on Mar. 26, 2014. Each of the above application(s) is hereby expressly incorporated by reference, in its entirety, into the present application.

BACKGROUND OF THE INVENTION

1. Field of the Invention

The present invention relates to a flexible tube for an endoscope in which an outer coating layer is formed so as to have multiple layers and a method for manufacturing the same.

2. Description of the Related Art

A flexible tube for an endoscope, which is a main part that forms an insertion unit of an endoscope inserted into the body of a subject, is formed by forming an outer coating layer by discharging a thermoplastic resin, such as an elastomer, to the outer peripheral surface of a flexible tube base while transporting the flexible tube base in a longitudinal direction (axial direction), the flexible tube base having a spiral tube formed by winding a metal strip in a spiral shape and a mesh tube covering the outer periphery of the spiral tube.

Since the insertion unit is inserted into a complicated and winding tube, such as a large intestine, ease of insertion is required for the flexible tube for an endoscope. For this reason, JP2009-106632A and JP2009-226023A disclose a flexible tube for an endoscope formed by forming a two-layer outer coating layer, which includes a soft resin layer and a hard resin layer that is harder than the soft resin layer, on the outer peripheral surface of a flexible tube base. In the outer coating layer formed so as to have two layers as described above, by changing the thickness ratio between the soft resin layer and the hard resin layer in the axial direction of the flexible tube for an endoscope, it is possible to change the flexibility in the axial direction of the flexible tube for an endoscope. In order to increase the flexibility in a distal portion of the flexible tube for an endoscope (make the distal portion soft) and reduce the flexibility in a proximal portion provided continuously to an operating unit (make the proximal portion hard), it is common to use a thickness ratio to reduce the thickness of the hard resin layer in the distal portion and increase the thickness of the hard resin layer in the proximal portion.

As a manufacturing method for forming the outer coating layer by changing the thickness ratio between the soft resin layer and the hard resin layer in the axial direction of the flexible tube for an endoscope, the amount of resin discharged to the outer peripheral surface of the flexible tube base is controlled by changing the rotation speed of the screw for extruding the molten resin. If the rotation speed of the screw is changed from high rotation speed to low rotation speed, the thickness of the resin layer to be coated is reduced. If the rotation speed of the screw is changed from low rotation speed to high rotation speed, the thickness of the resin layer to be coated is increased.

On the other hand, when the hard resin layer is used as an inner layer in the flexible tube for an endoscope in which the two-layer outer coating layer is formed using the manufacturing method described above, a portion with a small thickness near the distal end is especially influenced by the unevenness of the flexible tube base. As a result, a variation in the thickness of the hard resin layer occurs. When a variation in the thickness of the hard resin layer occurs, flexibility in the distal portion of the flexible tube for an endoscope is reduced. When the soft resin layer is formed as an outer layer in two-layer forming, dust or the like adheres easily, and the surface is easily scratched. Therefore, in the flexible tube for an endoscope disclosed in JP2009-226023A, the outer coating layer is formed by two-layer forming in which the soft resin layer is disposed on the inner side and the hard resin layer is disposed on the outer side.

In a flexible tube for an endoscope disclosed in JP2005-81100A and JP2004-141492A, a tapered portion is formed, for example, by polishing a hard resin layer located on the outer side of two layers that are formed, and the diameter of the distal side of the tapered portion is reduced and the diameter of the proximal side of the tapered portion is increased, thereby forming an outer coating layer. In a flexible tube for an endoscope disclosed in JP1989-212532A (JP-H01-212532A), a hard resin layer located on the inner side of two layers that are formed is covered from the middle of the outer peripheral surface of a flexible tube base, and a soft resin layer is uniformly formed on the flexible tube base and the outer side of the hard resin layer.

SUMMARY OF THE INVENTION

In order to further improve the flexibility of the flexible tube for an endoscope disclosed in JP2009-106632A and JP2009-226023A, it is considered to further increase the percentage of the thickness of the soft resin layer and further reduce the percentage of the thickness of the hard resin layer. However, even if the screw for extruding the resin is switched from high rotation speed to low rotation speed as much as possible in order to reduce the percentage of the thickness of the hard resin layer, it is difficult to reduce the amount of resin discharged to the flexible tube base because the pressure when extruding the resin at high rotation speed is applied to the resin. Therefore, there is a limit to the thickness ratio in two-layer forming. For this reason, even if the percentage of the thickness of the soft resin layer is set to the maximum and the percentage of the thickness of the hard resin layer is set to the minimum, there is a limit to flexibility. In addition, if the thickness of the entire outer coating layer is suppressed, unevenness of the flexible tube base is influenced. As a result, a variation in hardness occurs, or irregularities appear on the surface of the outer coating layer.

In addition, even if the tapered portion is provided in the middle of the hard resin layer located on the outer side of the two layers that are formed as disclosed in JP2005-81100A and JP2004-141492A, a hardness difference may be greatly changed before and after the tapered portion. This may lower the ease of insertion. In the flexible tube for an endoscope disclosed in JP1989-212532A (JP-H01-212532A), on the distal side of the flexible tube base where no hard resin layer is formed, insertion may be difficult.

The claimed invention has been made in view of the above problems, and it is an object of the claimed invention to provide a flexible tube for an endoscope that can improve the flexibility and the ease of insertion of a distal portion and a method for manufacturing the same.

A flexible tube for an endoscope according to an aspect of the invention includes a flexible tube base, an outer coating layer, and a ratio changing portion and a tapered portion that are formed in a outer coating layer. The flexible tube base has a spiral tube and a mesh tube. The spiral tube is formed by winding a metal strip in a spiral shape, and the mesh tube covers an outer periphery of the spiral tube. The outer coating layer is formed on an outer peripheral surface of the flexible tube base by two-layer forming, and includes a soft resin layer and a hard resin layer. The soft resin layer covers the outer peripheral surface of the flexible tube base. The hard resin layer covers an outer side of the soft resin layer using a resin that is harder than the soft resin layer. In the ratio changing portion, a percentage of a thickness of the hard resin layer with respect to a total thickness of the outer coating layer decreases and a percentage of a thickness of the soft resin layer with respect to the total thickness of the outer coating layer increases toward a distal side from a proximal side of the flexible tube base. The tapered portion is located on a distal side of the ratio changing portion. In the tapered portion, a ratio between the thickness of the hard resin layer and the thickness of the soft resin layer is maintained, which ratio is the same as that at a position in the ratio changing portion where the percentage of the thickness of the hard resin layer with respect to the total thickness of the outer coating layer is a lower limit. In the tapered portion, an outer diameter of the outer coating layer decreases toward a distal end of the flexible tube base so that a minimum outer diameter position matches a distal portion of the flexible tube base.

It is preferable that a thickness ratio between the soft resin layer and the hard resin layer in the tapered portion is 90:10 to 98:2. In addition, it is preferable that an outer diameter of the tapered portion is equal to or more than 10.5 mm and equal to or less than 12.8 mm and a difference between a maximum outer diameter and a minimum outer diameter is equal to or more than 0.04 mm and equal to or less than 0.3 mm. In addition, it is preferable that the tapered portion has a long shape in an axial direction in proportion to a magnitude of the outer diameter.

A method for manufacturing a flexible tube for an endoscope according to an aspect of the invention includes forming an outer coating layer, which includes a soft resin layer covering an outer peripheral surface of a flexible tube base and a hard resin layer covering an outer side of the soft resin layer, on an entire peripheral surface around an axis of the flexible tube base by extrusion by supplying a soft resin and a hard resin in a molten state disposed outside a forming passage to the forming passage while transporting the flexible tube base along an axial direction from a proximal side to a distal side in the forming passage. The method for manufacturing a flexible tube for an endoscope further includes: forming a ratio changing portion by decreasing a percentage of a thickness of the hard resin layer with respect to a total thickness of the outer coating layer and increasing a percentage of a thickness of the soft resin layer with respect to the total thickness of the outer coating layer by increasing the soft resin supplied to the forming passage and decreasing the hard resin supplied to the forming passage while transporting the flexible tube base at a fixed transport speed; and forming a tapered portion, in which an outer diameter of the outer coating layer decreases toward a distal end of the flexible tube base, by increasing a transport speed gradually from a transport speed of forming the ratio changing portion, while maintaining a ratio between the thickness of the hard resin layer and the thickness of the soft resin layer that is the same as that at a position in the ratio changing portion where the percentage of the thickness of the hard resin layer with respect to the total thickness of the outer coating layer is a lower limit.

In the endoscope according to the aspect of the invention, the tapered portion is formed which is located on the distal side of the ratio changing portion and in which the same thickness ratio as that at a position in the ratio changing portion where the percentage of the thickness of the soft resin layer is the maximum is maintained and the minimum outer diameter position matches the distal portion of the flexible tube base as a result of a decrease in the outer diameter of the outer coating layer toward the distal side of the flexible tube base. Accordingly, it is possible to improve the flexibility of the distal portion of the flexible tube for an endoscope.

DESCRIPTION OF THE PREFERRED EMBODIMENTS

Figure 1:
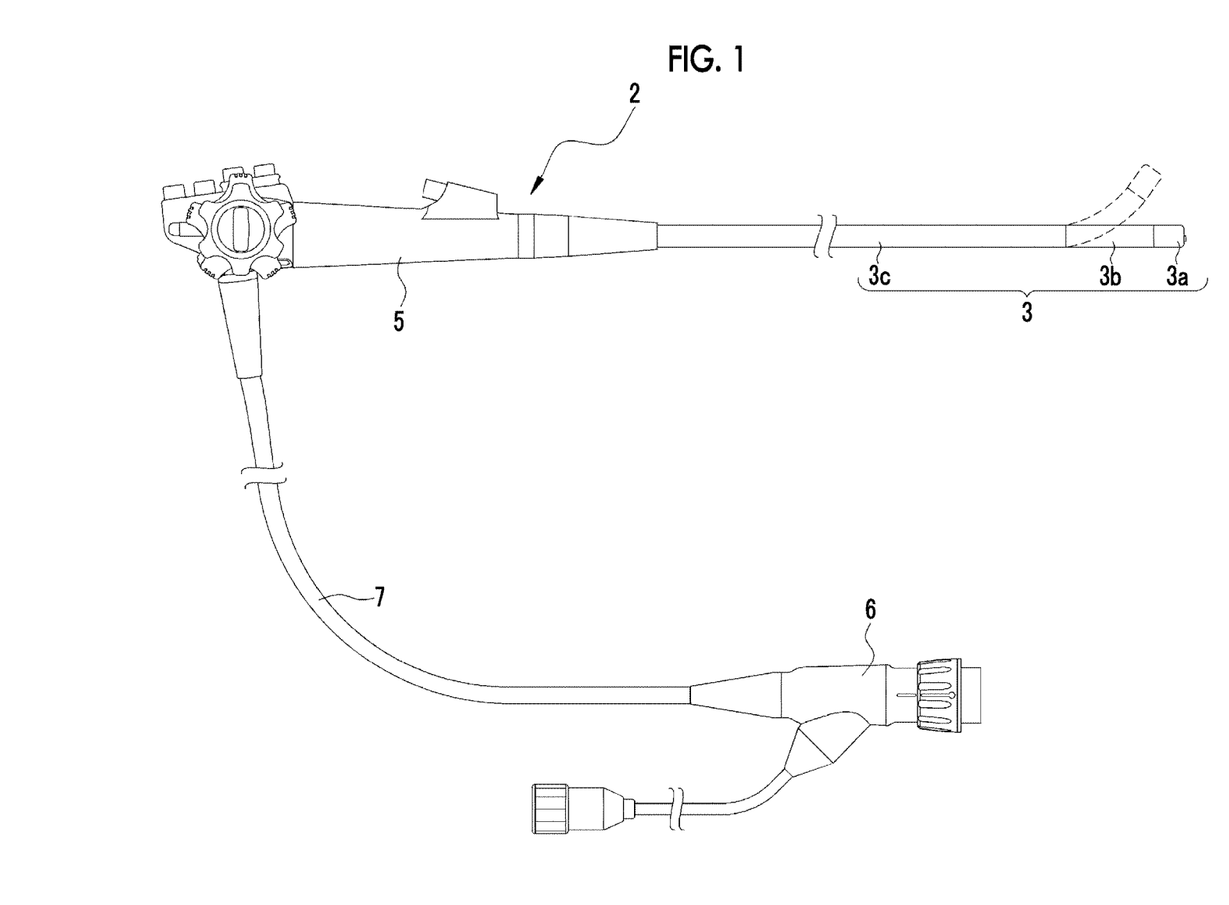
FIG. 1 is an external view showing the configuration of an electronic endoscope.

As shown in FIG. 1, an electronic endoscope 2 includes an insertion unit 3 that is inserted into a body cavity, an operating unit 5 provided continuously to a proximal portion of the insertion unit 3, a connector 6 connected to a processor device or a light source device, and a universal cord 7 for connecting the operating unit 5 and the connector 6 to each other.

The insertion unit 3 includes a distal portion 3a, a bending portion 3b, and a soft portion 3c in order from the distal end. A camera unit (not shown) for imaging the inside of a subject is built into the distal portion 3a. The bending portion 3b is provided continuously to the proximal end of the distal portion 3a, and is configured to freely bend. The soft portion 3c occupies the length of the majority of the insertion unit 3, and is flexible over approximately the entire length. In particular, a portion inserted into the inside, such as a body cavity, has a more flexible structure.

Figure 2:
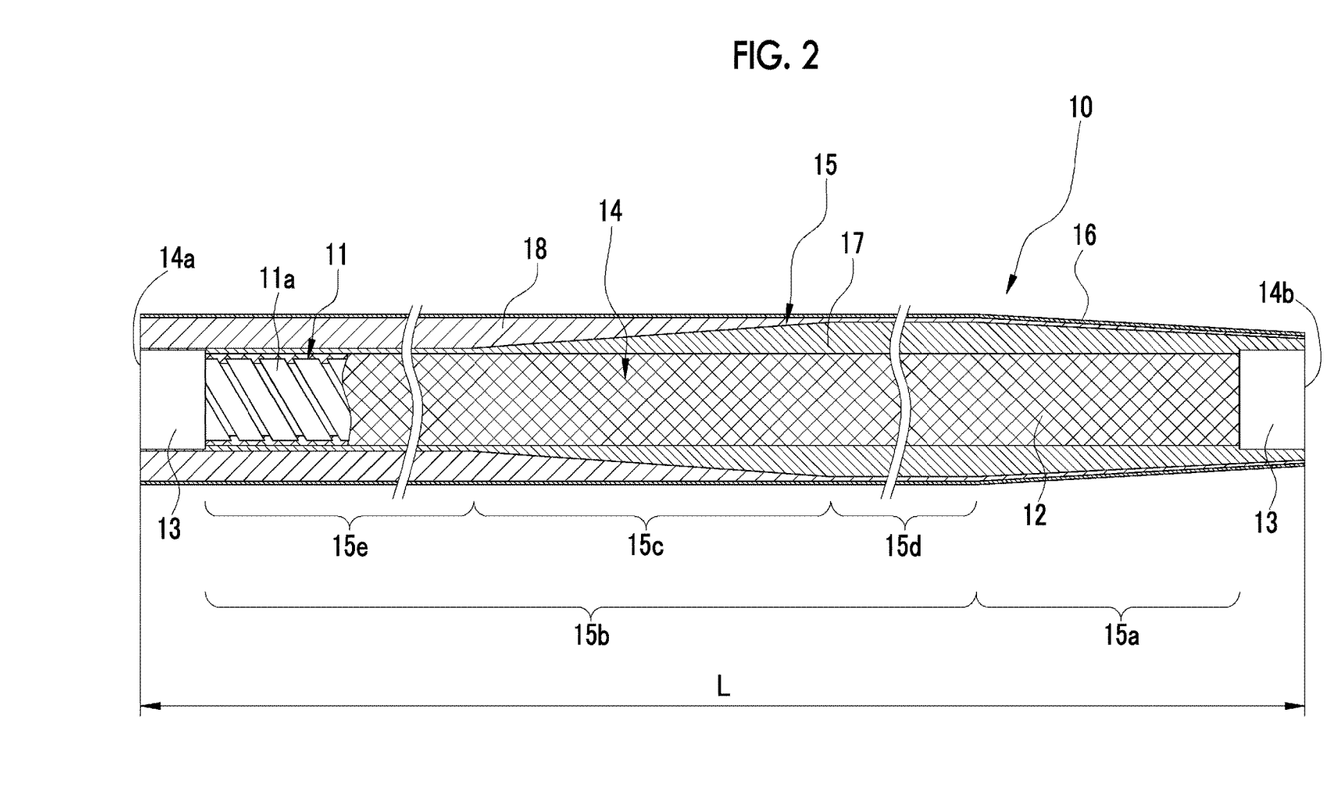
FIG. 2 is a partial sectional view showing the schematic configuration of a flexible tube for an endoscope.

As shown in FIG. 2, a flexible tube for an endoscope (hereinafter, referred to as a flexible tube) 10 that forms the soft portion 3c is formed by covering an outer coating layer 15, which is formed of resin, on the outer peripheral surface of a flexible tube base 14. The flexible tube base 14 is formed by covering a mesh tube 12, which is formed by braiding the metal wire, on a spiral tube 11, which is formed by winding a metal strip 11a in a spiral shape on the innermost side, and fitting a cap 13 at both ends. In addition, a chemical-resistant coating film 16 containing, for example, fluorine is coated on the outer surface of the outer coating layer 15. In order to clearly illustrate the layer structure, the outer coating layer 15 and the coating film 16 are drawn thicker than the diameter of the flexible tube base 14.

The outer coating layer 15 covers the outer peripheral surface of the flexible tube base 14. The outer coating layer 15 has a two-layer structure obtained by laminating a soft resin layer 17 that covers the outer peripheral surface of the flexible tube base 14 and a hard resin layer 18 that covers the outer peripheral surface of the soft resin layer 17. A soft resin is used as a material of the soft resin layer 17, and a hard resin that is harder than the soft resin layer 17 is used as a material of the hard resin layer 18. As the resin used for the soft resin layer 17 and the hard resin layer 18, for example, two types of thermoplastic urethane elastomers having different hardnesses are used.

The outer coating layer 15 has a tapered portion 15a and a large diameter portion 15b in order from the distal end of the flexible tube base 14. The large diameter portion 15b is formed with an approximately uniform thickness in the longitudinal direction (axial direction) of the flexible tube base 14. The large diameter portion 15b includes a ratio changing portion 15c and ratio fixed portions 15d and 15e located on the distal side and proximal side of the ratio changing portion 15c.

Figure 3:
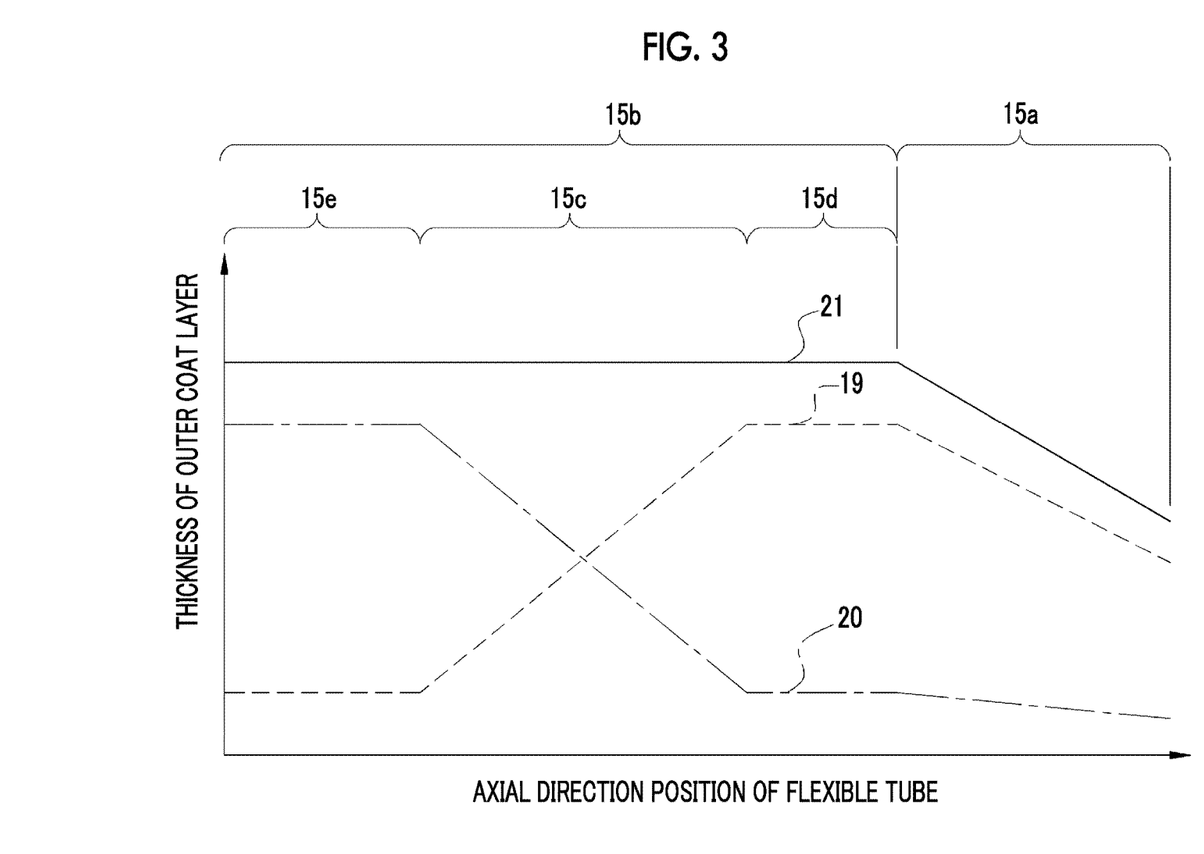
FIG. 3 is a graph showing the thickness of an outer coating layer.

FIG. 3 is a diagram conceptually showing the thickness of the soft resin layer 17, the hard resin layer 18, and the outer coating layer 15 formed in the flexible tube base 14. The broken line 19 indicates the thickness of the soft resin layer 17 (refer to FIG. 2), the one-dot chain line 20 indicates the thickness of the hard resin layer 18 (refer to FIG. 2), and the solid line 21 indicates the thickness of the outer coating layer 15 (refer to FIG. 2). In the ratio changing portion 15c, the thickness of the soft resin layer 17 increases gradually and the thickness of the hard resin layer 18 decreases gradually from the proximal end 14a side toward the distal end 14b side of the flexible tube base 14. The ratio fixed portion 15d has a thickness ratio in which the thickness of the soft resin layer 17 is large and the thickness of the hard resin layer 18 is small, and the ratio fixed portion 15e has a thickness ratio in which the thickness of the hard resin layer 18 is large and the thickness of the soft resin layer 17 is small. In the ratio changing portion 15c, the thickness of the soft resin layer 17 and the hard resin layer 18 changes from the same thickness ratio as the ratio fixed portion 15e to the same thickness ratio as the ratio fixed portion 15d.

The tapered portion 15a has the same thickness ratio as that at a position in the ratio changing portion 15c where the percentage of the thickness of the hard resin layer 18 is a lower limit. In addition, the outer diameter of the tapered portion 15a decreases gradually toward the distal end 14b side of the flexible tube base 14 and the minimum outer diameter position matches the distal portion of the flexible tube base 14 while maintaining the same thickness ratio as the ratio fixed portion 15d. The tapered portion 15a has the same outer diameter as the large diameter portion 15b at the maximum outer diameter position adjacent to the large diameter portion 15b. Accordingly, in the flexible tube 10, the flexibility of the distal portion of the large diameter portion 15b is higher than that of the proximal portion, and the flexibility increases toward the distal side of the tapered portion 15a from the proximal side more than the distal portion of the large diameter portion 15b. The flexibility is the highest in the distal portion where the outer diameter of the tapered portion 15a is the minimum. In addition, a portion having high flexibility in the flexible tube 10 is limited to a flexible portion in the flexible tube base 14, and the cap 13 that is not flexible and the outer coating layer 15 covered by the cap 13 are not included.

The total length L of the flexible tube 10 in the axial direction is 1700 mm, for example, and the tapered portion 15a is formed at a position of equal to or more than 100 mm and equal to or less than 400 mm from the distal end 14b of the flexible tube base 14. The ratio changing portion 15c is formed closer to the proximal side than the tapered portion 15a, and is formed at a position of equal to or more than 700 mm and equal to or less than 1100 mm from the distal end 14b of the flexible tube base 14. The maximum outer diameter of the tapered portion 15a is equal to or more than 10.5 mm and equal to or less than 12.8 mm. Since the maximum thickness of the outer coating layer 15 increases as the maximum outer diameter of the tapered portion 15a increases, it is difficult to realize the flexibility near the distal portion. Therefore, in terms of flexibility, it is preferable to form the tapered portion 15a long in the axial direction in proportion to the magnitude of the maximum outer diameter.

In the tapered portion 15a, there is a difference of equal to or more than 0.04 mm and equal to or less than 0.3 mm between the maximum outer diameter and the minimum outer diameter. The outer diameter difference is a difference in the thickness of the outer coating layer 15. Accordingly, for the thickness of the outer coating layer 15 in the tapered portion 15a, there is a difference of equal to or more than 0.02 mm and equal to or less than 0.15 mm between the distal end and the proximal end.

The thickness of the outer coating layer 15 in the large diameter portion 15b, that is, the thickness of the outer coating layer 15 at the maximum outer diameter position of the tapered portion 15a is 400 µm, for example. The thickness ratio between the soft resin layer 17 and the hard resin layer 18 in the tapered portion 15a is set to 95:5 to 97:3. For the thickness ratio between the soft resin layer 17 and the hard resin layer 18 in the tapered portion 15a, it is possible to reduce the percentage of the thickness of the hard resin layer 18 and increase the percentage of the thickness of the soft resin layer 17 according to the total thickness of the outer coating layer 15 in the large diameter portion 15b. In addition, the thickness of the outer coating layer 15 in the large diameter portion 15b and the thickness ratio between the soft resin layer 17 and the hard resin layer 18 in the tapered portion 15a are not limited to those described above. It is preferable to set the thickness of the outer coating layer 15 in the large diameter portion 15b to equal to or more than 200 and equal to or less than 800 µm, and it is preferable to set the thickness ratio between the soft resin layer 17 and the hard resin layer 18 in the tapered portion 15a to 90:10 to 98:2.

In addition, the resin used for the soft resin layer 17 and the hard resin layer 18 is not limited to those described above, and it is possible to use various resins according to the desired performance. For example, when it is necessary to change the elastic force in the soft resin layer 17 and the hard resin layer 18, it is preferable to use polyester-based elastomers, polystyrene-based elastomers, and polyurethane-based elastomers. When it is necessary to change the chemical resistance in the soft resin layer 17 and the hard resin layer 18, it is preferable to use polyolefin-based elastomers, polyamide-based elastomers, and fluorine-based elastomers.

Two types of resins used for the soft resin layer 17 and the hard resin layer 18 may change various physical properties, such as insulation and surface slipperiness, as well as the hardness, elastic force, and chemical resistance. The physical properties may be changed using resins having different compositions, or may be changed using resins of the same type having different densities.

Figure 4:
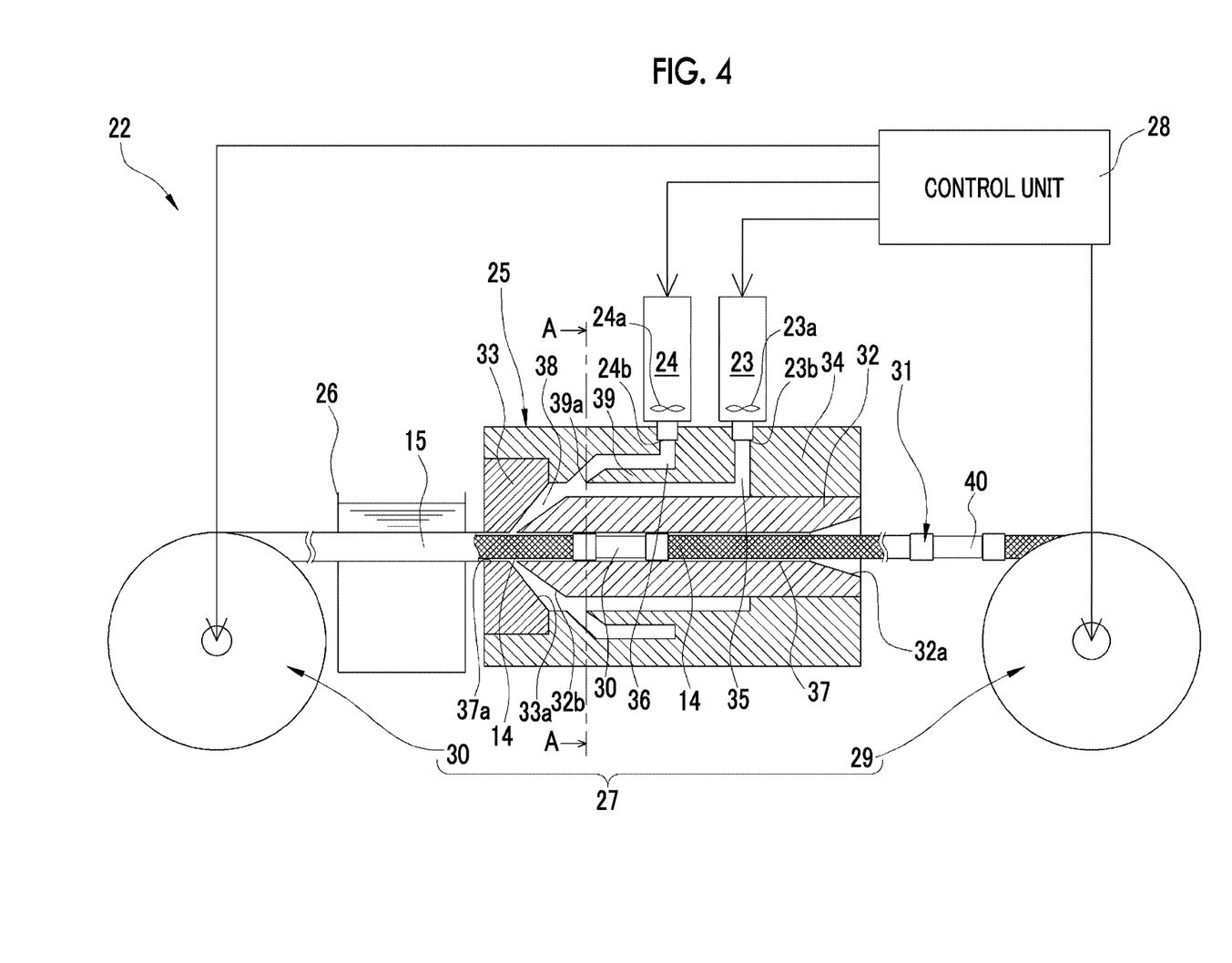
FIG. 4 is a block diagram schematically showing the configuration of a continuous forming machine for manufacturing the flexible tube for an endoscope.

Hereinafter, a method for manufacturing the flexible tube 10 having the above configuration will be described. In FIG. 4 which shows the configuration of a continuous forming machine 22 for forming the outer coating layer 15, the continuous forming machine 22 includes extrusion units 23 and 24, a head unit 25 for forming the outer coating layer 15 on the outer peripheral surface of the flexible tube base 14 by coating, a cooling unit 26, a transport unit 27 for transporting a flexible tube base for connection 31 to be described later to the head unit 25, and a control unit 28 that controls these. The extrusion units 23 and 24 have a known configuration including a hopper, screws 23a and 24a, and the like.

The transport unit 27 is configured to include a supply drum 29 and a winding drum 30, and the flexible tube base for connection 31 that connects a plurality of flexible tube bases 14 to each other is wound around the supply drum 29. After being wound around the supply drum 29, the flexible tube base for connection 31 is sequentially pulled out to be wound around the winding drum 30 through the head unit 25 that forms the outer coating layer 15 and the cooling unit 26 that cools the outer coating layer 15 after forming. The rotation speed of the supply drum 29 and the winding drum 30 is controlled by the control unit 28, so that the transport speed for transporting the flexible tube base for connection 31 is changed.

The head unit 25 is configured to include a nipple 32, a die 33, and a support 34 to fixedly support these. Gates 35 and 36 for transporting hard resin and soft resin in a molten state, which are extruded from the extrusion units 23 and 24, to a resin passage 38 are formed in the support 34.

In each of the nipple 32 and the die 33, a forming passage 37 is formed so as to penetrate the approximate center. The forming passage 37 is a passage through which the flexible tube base for connection 31 transported in the axial direction by the transport unit 27 passes, and has a circular cross-sectional shape perpendicular to the axial direction. The forming passage 37 is connected to a discharge port corresponding to the downstream end of the resin passage 38, and the resin in a molten state is supplied to the forming passage 37 from the resin passage 38.

The resin passage 38 is formed by the space interposed between the nipple 32 and the die 33. A conical protrusion 32b that forms the resin passage 38 together with a conical recess 33a located at the right end of the die 33 is formed at the left end of the nipple 32 in FIG. 4. In addition, a conical recess 32a that is provided continuously to the rear end of the forming passage 37 in order to guide the insertion of the flexible tube base for connection 31 is formed.

An exit hole 37a of the forming passage 37 is formed in the die 33. The flexible tube base for connection 31 on which the outer coating layer 15 is coated is transported to the cooling unit 26 after passing through the exit hole 37a. Coolant, such as water, is stored in the cooling unit 26, and the outer coating layer 15 is cooled and hardened after passing through the coolant. The outer coating layer 15 may also be cooled by blowing the coolant, air, or the like thereto without being limited to the above.

The resin passage 38 is disposed outside the forming passage 37, and the cross-sectional shape of the resin passage 38 perpendicular to the axial direction of the forming passage 37 is a circular shape that forms concentric circles together with the forming passage 37. The discharge port of the resin passage 38 is connected to the entire circumference of the forming passage 37 in the circumferential direction. Accordingly, resin in a molten state is discharged to the entire peripheral surface of the flexible tube base for connection 31 passing through the discharge port of the resin passage 38.

In the extrusion units 23 and 24, discharge ports 23b and 24b are connected to the gates 35 and 36 of the head unit 25, respectively. Therefore, soft resin and hard resin in a molten state, which are materials of the soft resin layer 17 and the hard resin layer 18, are extruded and supplied to the forming passage 37 of the head unit 25 through the resin passage 38. By controlling the rotation speed of each of the screws 23a and 24a using the control unit 28, the amount of discharge of each of the soft resin and the hard resin in a molten state that are discharged from the extrusion units 23 and 24 is adjusted.

Not only is the temperature of each of the soft resin and the hard resin increased by heating the extrusion units 23 and 24 and the head unit 25, but also the temperature of each of the soft resin and the hard resin is increased by increasing the rotation speed of each of the screws 23a and 24a. Thus, the fluidity is increased.

Both of the gates 35 and 36 are disposed outside the forming passage 37, and the gate 36 is disposed outside the gate 35. Each of the gates 35 and 36 is an approximately cylindrical passage having a circular cross-sectional shape perpendicular to the axial direction of the forming passage 37. Downstream ends of the gates 35 and 36 in the transport direction of soft resin and hard resin are connected to the upstream end of the resin passage 38. This connection portion is a merging portion where soft resin and hard resin merge with each other. Between the gates 35 and 36, a separating portion 39 for separating the gates 35 and 36 from each other is provided.

In the separating portion 39, an edge 39a is disposed in the merging portion in order to separate the gates 35 and 36 from each other on the upstream side of the merging portion. Soft resin and hard resin transported from the gates 35 and 36 merge with each other after passing through the edge 39a. The edge 39a is tapered toward the distal end in order to merge the two types of resins.

In the merging portion, the soft resin in a molten state supplied from the gate 35 and the hard resin in a molten state supplied from the gate 36 merge so as to overlap each other in a state where the soft resin is located on the inner side and the hard resin is located on the outer side. The soft resin and the hard resin that have merged with each other flow through the resin passage 38 in the overlapping state. The soft resin and the hard resin are discharged toward the entire circumference of the flexible tube base for connection 31 from the discharge port connected to the entire circumference of the forming passage 37 in the circumferential direction while maintaining the overlapping state. Therefore, the outer coating layer 15 having two layers of the soft resin layer 17 that covers the outer peripheral surface of the flexible tube base 14 and the hard resin layer 18 that covers the outer side of the soft resin layer 17 is formed on the entire peripheral surface around the axis of the flexible tube base 14.

Figure 5:
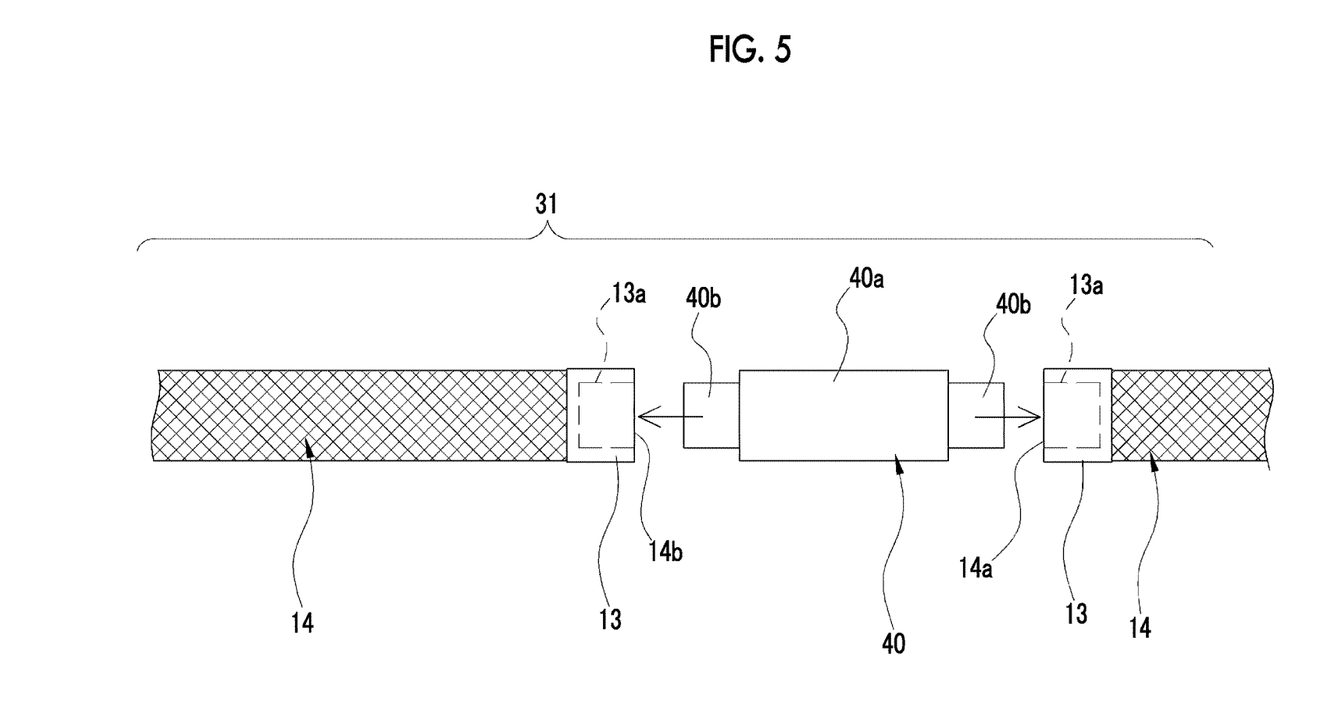
FIG. 5 is an explanatory view showing a flexible tube base for connection formed by connecting a plurality of flexible tube bases to each other.

Before the step of forming the outer coating layer 15 on the flexible tube base 14 in the continuous forming machine 22, the flexible tube base for connection 31 is prepared using a joint member 40 as shown in FIG. 5. The joint member 40 includes a main body portion 40a and connecting portions 40b that are located on both sides of the main body portion 40a and are inserted into the cap 13 along an inner peripheral surface 13a of the cap 13. As the flexible tube base for connection 31 in a state where a plurality of flexible tube bases 14 are connected to each other as one body through the joint member 40, forming of the outer coating layer 15 is performed in the continuous forming machine 22.

The outer diameter of the main body portion 40a of the joint member 40 is smaller than the outer diameter of the flexible tube base 14. Without being limited to the above, the diameter of at least a part of the joint member 40 may be smaller than the diameter of the flexible tube base 14. The surface of the joint member 40 is coated with a release material, such as Teflon (registered trademark), so that the outer coating layer 15 formed on the outer peripheral surface of the joint member 40 is easily peeled off after the outer coating layer 15 is formed as the flexible tube base for connection 31. The main body portion 40a of the joint member 40 has flexibility. In order to return the thickness ratio and the total thickness of resin during the forming of the outer coating layer 15 in the main body portion 40a, the main body portion 40a is formed in a length in consideration of the balance between the transport speed in continuous forming and the amount of supply of resin. As the flexible tube base for connection 31, the claimed invention is not limited to that described above. For example, it is possible to use a joint member for connecting the flexible tube base 14 using a screw.

When performing the forming process in the continuous forming machine 22, soft resin and hard resin in a molten state are extruded from the extrusion units 23 and 24 to the head unit 25, and the transport unit 27 is operated to transport the flexible tube base for connection 31 through the forming passage 37. Regarding a direction of the transport of the flexible tube base for connection 31 by the transport unit 27, the flexible tube base for connection 31 is transported from the proximal end 14a of the flexible tube base 14 to the forming passage 37. The extrusion units 23 and 24 extrude the soft resin and the hard resin so as to be supplied to the head unit 25 at all times. The soft resin and the hard resin extruded from the extrusion units 23 and 24 to the gates 35 and 36 pass through the edge 39a and merge with each other, and are supplied to the forming passage 37 through the resin passage 38 in the overlapping state. As a result, the outer coating layer 15 having two layers is continuously formed.

Figure 6:
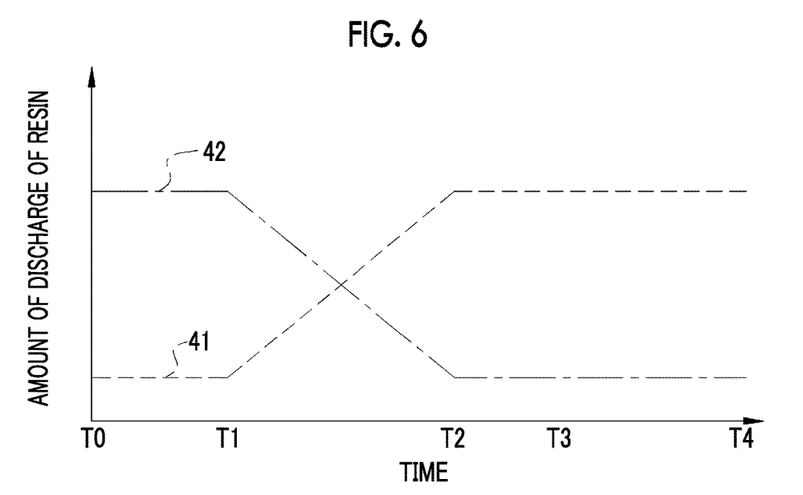
FIG. 6 is a graph showing the control of the amount of discharge of soft resin and hard resin using extrusion units.
Figure 7:
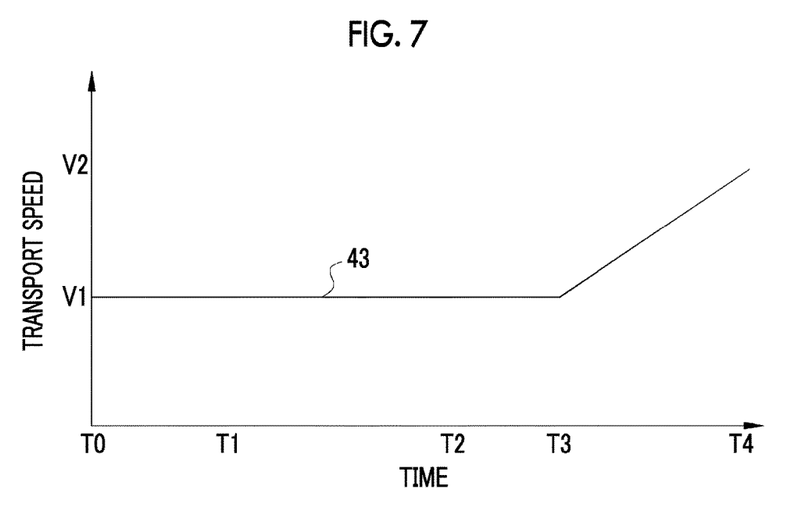
FIG. 7 is a graph showing the control of the transport speed of the flexible tube base for connection using a transport unit.

In the continuous forming machine 22, the amount of discharge of each of the soft resin and the hard resin that are discharged from the extrusion units 23 and 24 is controlled (refer to FIG. 6), and the transport speed of the flexible tube base for connection 31 transported by the transport unit 27 is controlled (refer to FIG. 7). Accordingly, it is possible to change the thickness ratio between the soft resin layer 17 and the hard resin layer 18 and to change the thickness (total thickness of the soft resin layer 17 and the hard resin layer 18) of the outer coating layer 15. Reference numeral T0 indicates a time to start the forming of the outer coating layer 15 from the proximal end of the flexible tube base 14, and reference numeral T4 indicates a time to end the forming of the outer coating layer 15 up to the distal portion of the flexible tube base 14.

As shown in FIG. 6, for the control of the extrusion units 23 and 24, first, from time T0 to time T1, soft resin and hard resin are discharged from the extrusion units 23 and 24 with a fixed amount in which the amount of discharge of the hard resin is larger than the amount of discharge of the soft resin. The broken line 41 indicates the amount of discharge of soft resin using the extrusion unit 23, and the one-dot chain line 42 indicates the amount of discharge of hard resin using the extrusion unit 24. Then, from time T1 to time T2, the amount of discharge of the soft resin using the extrusion unit 23 is gradually increased, and the amount of discharge of the hard resin using the extrusion unit 24 is gradually decreased. At time T2, the amount of discharge of the soft resin becomes larger than the amount of discharge of the hard resin. Then, from time T2 to time T4, the soft resin and the hard resin are discharged from the extrusion units 23 and 24 with a fixed amount in which the amount of discharge of the soft resin is larger than the amount of discharge of the hard resin. In addition, the total amount of discharge of the soft resin and the hard resin using the extrusion units 23 and 24 are always the same. Thus, when forming the outer coating layer 15 from the proximal end 14a side to the distal end 14b side of the flexible tube base 14, the outer coating layer 15 is formed at a fixed thickness ratio in which the percentage of the thickness of the hard resin layer 18 is large and the percentage of the thickness of the soft resin layer 17 is small from time T0 to time T1, and the percentage of the thickness of the soft resin layer 17 increases gradually and the percentage of the thickness of the hard resin layer 18 decreases gradually from the proximal end 14a side toward the distal end 14b side from time T1 to time T2. Then, from time T2 to time T4, the outer coating layer 15 is formed at a fixed thickness ratio in which the percentage of the thickness of the soft resin layer 17 is large and the percentage of the thickness of the hard resin layer 18 is small.

On the other hand, as shown in FIG. 7, for the control of the transport unit 27, the flexible tube base for connection 31 is transported at a fixed transport speed V1 from time T0 to time T3. The solid line 43 indicates a change in the transport speed of the flexible tube base for connection 31 by the transport unit 27. Time T3 is set between the time T2 and the time T4 described above. Then, from time T3 to time T4, the transport speed is gradually increased from V1 to V2. When forming the outer coating layer 15 from the proximal end 14a side to the distal end 14b side of the flexible tube base 14, the large diameter portion 15b in which the total thickness of the soft resin layer 17 and the hard resin layer 18 is fixed is formed from time T0 to time T3, and the total thickness of the soft resin layer 17 and the hard resin layer 18 laminated on the flexible tube base 14 is gradually decreased to form the tapered portion 15a from time T3 to time T4.

As described above, the thickness ratio between the soft resin and the hard resin is fixed from time T0 to time T1, changes from time T1 to time T2, and is fixed from time T2 to time T4. Therefore, the ratio fixed portion 15e, the ratio changing portion 15c, and the ratio fixed portion 15d are formed in the large diameter portion 15b. In the tapered portion 15a formed from time T3 to time T4, the outer diameter decreases gradually toward the distal end 14b side of the flexible tube base 14 while maintaining the same thickness ratio as the ratio fixed portion 15d.

In the continuous forming machine 22, the amount of discharge of the hard resin discharged to the forming passage 37 is decreased and the amount of discharge of the soft resin discharged to the forming passage 37 is increased by switching the screw 24a of the extrusion unit 24 to low rotation speed from high rotation speed and switching the screw 23a of the extrusion unit 23 to high rotation speed from low rotation speed. However, even if the screw 24a is switched to low rotation speed as much as possible, pressure when extruding the hard resin at high rotation speed remains. For this reason, there is a limit in reducing the amount of discharge of the hard resin. Accordingly, there is a lower limit to the percentage of the thickness of the hard resin layer 18. In the present embodiment, therefore, control to reduce the percentage of the thickness of the hard resin layer 18 to the lower limit is performed at time T2 at a thickness ratio in which the percentage of the thickness of the soft resin layer 17 in the ratio changing portion 15c is the largest and the percentage of the thickness of the hard resin layer 18 in the ratio changing portion 15c is the smallest. As described above, in the present embodiment, when reducing the percentage of the thickness of the hard resin layer 18 to the lower limit, the thickness ratio between the soft resin layer 17 and the hard resin layer 18 is set to 95:5 to 97:3. Also for the ratio fixed portion 15d and the tapered portion 15a, the same thickness ratio as that at a position where the percentage of the thickness of the hard resin layer 18 is reduced to the lower limit is maintained to form the outer coating layer 15.

In this forming step, the outer coating layer 15 is continuously formed on the plurality of flexible tube bases 14 while the flexible tube base for connection 31 is being transported through the forming passage 37. Therefore, in the continuous forming machine 22, control of the amount of discharge of the soft resin and the hard resin described above and the transport speed of the flexible tube base for connection 31 is repeated. That is, after performing the control from time T0 to time T4 shown in FIGS. 6 and 7, when the proximal end 14a of the next flexible tube base 14 reaches the forming start position of the outer coating layer 15, control for returning to the amount of discharge and the transport speed at time T0 is performed. Then, the amount of discharge by the extrusion units 23 and 24 and the speed of transport by the transport unit 27 are similarly controlled, thereby forming the outer coating layer 15 on the flexible tube base for connection 31.

The flexible tube base for connection 31 on which the outer coating layer 15 has been formed up to the last end is detached from the continuous forming machine 22. Then, the joint member 40 is detached from the flexible tube base 14 for separation into each flexible tube base 14. Then, for the separated flexible tube base 14, the coating film 16 is coated on the outer coating layer 15. Thus, the flexible tube 10 is completed. The completed flexible tube 10 is transported for the assembly process of the electronic endoscope 2.

As described above, in the flexible tube 10, the outer coating layer 15 includes the tapered portion 15a in which the thickness ratio, which is the same as that at a position in the ratio changing portion 15c where the percentage of the thickness of the hard resin layer 18 is a lower limit, is maintained and the position of the minimum outer diameter matches the distal portion of the flexible tube base 14 as a result of a gradual decrease in the outer diameter toward the distal end. Accordingly, it is possible to improve the flexibility of the distal portion of the flexible tube 10. In a known flexible tube, even if the percentage of the thickness of the hard resin layer is set to the lower limit, the flexibility of the distal portion is not sufficient because the outer coating layer having a uniform thickness is formed. In the present embodiment, however, the flexibility of the distal portion is sufficient. In addition, since the minimum outer diameter position of the tapered portion 15a is located at the distal portion of the flexible tube 10, the flexibility is improved gradually toward the distal end, and the ease of insertion of the insertion unit 3 is improved.

In the embodiment described above, the ratio fixed portion 15d is formed between the ratio changing portion 15c and the tapered portion 15a. However, the claimed invention is not limited thereto, and it is possible to form the outer coating layer 15 in which the ratio changing portion 15c and the tapered portion 15a are adjacent to each other. When forming the outer coating layer 15 in which the ratio changing portion 15c and the tapered portion 15a are adjacent to each other, it is preferable to perform control to maintain the transport speed V1 from time T0 to time T2, at which the percentage of the thickness of the soft resin layer 17 is the largest and the percentage of the thickness of the hard resin layer 18 is the smallest, and increase the transport speed gradually from V1 to V2 from time T2.

In addition, although the two-layer forming has been described as an example in the above embodiment, the outer coating layer may be configured to have multiple layers of two or more layers. For example, an intermediate layer may be formed between the hard resin layer and the soft resin layer.

In the above embodiment, an electronic endoscope for observing an image obtained by capturing the inside of the body of the subject using a camera unit has been described as an example. However, the claimed invention is not limited thereto, and can also be applied to an endoscope for observing the state of the inside of the body of the subject by adopting the optical image guide.

While the preferred embodiment of the claimed invention has been described in detail, the claimed invention is not limited to the specific embodiment described above, and various changes and modifications can be made within the scope of the claimed invention as defined in the appended claims.

What is claimed is:

1. A flexible tube for an endoscope, comprising:
   a flexible tube base including: a spiral tube formed by winding a metal strip in a spiral shape; and a mesh tube covering an outer periphery of the spiral tube;
   an outer coating layer that is formed on an outer peripheral surface of the flexible tube base by two-layer forming and that includes a soft resin layer and a hard resin layer, the soft resin layer covering the outer peripheral surface of the flexible tube base, and the hard resin layer covering an outer side of the soft resin layer using a resin that is harder than the soft resin layer;
   a ratio changing portion which is formed in the outer coating layer and in which a percentage of a thickness of the hard resin layer with respect to a total thickness of the outer coating layer decreases and a percentage of a thickness of the soft resin layer with respect to the total thickness of the outer coating layer increases toward a distal side from a proximal side of the flexible tube base; and
   a tapered portion which is formed in the outer coating layer and is located on a distal side of the ratio changing portion, and in which tapered portion a ratio between the thickness of the hard resin layer and the thickness of the soft resin layer is maintained, which ratio between the thickness of the hard resin layer and the thickness of the soft resin layer is the same as that at a position in the ratio changing portion where the percentage of the thickness of the hard resin layer with respect to the total thickness of the outer coating layer is a lower limit, and in which tapered position an outer diameter of the outer coating layer decreases toward a distal end of the flexible tube base so that a minimum outer diameter position matches a distal portion of the flexible tube base,
   wherein in the tapered portion, each thickness of the hard resin layer and soft resin layer decreases toward a distal end of the flexible tube base.

2. The flexible tube for an endoscope according to claim 1, wherein a thickness ratio between the soft resin layer and the hard resin layer in the tapered portion is 90:10 to 98:2.

3. The flexible tube for an endoscope according to claim 1,
wherein a maximum outer diameter of the tapered portion is equal to or more than 10.5 mm and equal to or less than 12.8 mm, and
a difference between the maximum outer diameter and a minimum outer diameter is equal to or more than 0.04 mm and equal to or less than 0.3 mm.

4. The flexible tube for an endoscope according to claim 2,
wherein a maximum outer diameter of the tapered portion is equal to or more than 10.5 mm and equal to or less than 12.8 mm, and
a difference between the maximum outer diameter and a minimum outer diameter is equal to or more than 0.04 mm and equal to or less than 0.3 mm.

5. The flexible tube for an endoscope according to claim 1,
wherein the tapered portion has a long shape in an axial direction in proportion to a magnitude of a maximum outer diameter.

6. The flexible tube for an endoscope according to claim 2,
wherein the tapered portion has a long shape in an axial direction in proportion to a magnitude of a maximum outer diameter.

7. The flexible tube for an endoscope according to claim 3,
wherein the tapered portion has a long shape in an axial direction in proportion to a magnitude of a maximum outer diameter.

8. The flexible tube for an endoscope according to claim 4,
wherein the tapered portion has a long shape in an axial direction in proportion to a magnitude of a maximum outer diameter.

9. The flexible tube for an endoscope according to claim 1, further comprising:
a ratio fixed portion which is located on a proximal side of the tapered portion and on a distal side of the ratio changing portion, in which radio fixed portion a ratio between the thickness of the hard resin layer and the thickness of the soft resin layer is maintained, and which is formed with an approximately uniform thickness of the outer coating layer.

10. A method for manufacturing a flexible tube for an endoscope, comprising:
forming an outer coating layer, which includes a soft resin layer covering an outer peripheral surface of a flexible tube base and a hard resin layer covering an outer side of the soft resin layer, on an entire peripheral surface around an axis of the flexible tube base by extrusion by supplying a soft resin and a hard resin in a molten state disposed outside a forming passage to the forming passage while transporting the flexible tube base along an axial direction from a proximal side to a distal side in the forming passage;
forming a ratio changing portion by decreasing a percentage of a thickness of the hard resin layer with respect to a total thickness of the outer coating layer and increasing a percentage of a thickness of the soft resin layer with respect to the total thickness of the outer coating layer by increasing the soft resin supplied to the forming passage and decreasing the hard resin supplied to the forming passage while transporting the flexible tube base at a fixed transport speed; and
forming a tapered portion, in which an outer diameter of the outer coating layer decreases toward a distal end of the flexible tube base, by increasing a transport speed gradually from a transport speed of forming the ratio changing portion, while maintaining a ratio between the thickness of the hard resin layer and the thickness of the soft resin layer that is the same as that at a position in the ratio changing portion where the percentage of the thickness of the hard resin layer with respect to the total thickness of the outer coating layer is a lower limit.

* * * * *